(12) United States Patent
McLusky et al.

(10) Patent No.: US 12,708,717 B2
(45) Date of Patent: Aug. 18, 2026

(54) CAP FOR AN INJECTION DEVICE

(71) Applicant: Janssen Pharmaceuticals, Inc., Titusville, NJ (US)

(72) Inventors: James McLusky, Edinburgh (GB); Nick Foley, Edinburgh (GB); Jimmy Mower, Edinburgh (GB); Michael Cannamela, Atlantic Highlands, NJ (US); Peter Krulevitch, Pleasanton, CA (US); James Flint, Hillsborough, NJ (US)

(73) Assignee: JANSSEN PHARMACEUTICALS, INC., Titusville, NJ (US)

(*) Notice: Subject to any disclaimer, the term of this patent is extended or adjusted under 35 U.S.C. 154(b) by 963 days.

(21) Appl. No.: 17/057,446

(22) PCT Filed: May 29, 2018

(86) PCT No.: PCT/US2018/034852
§ 371 (c)(1),
(2) Date: Nov. 20, 2020

(87) PCT Pub. No.: WO2019/231432
PCT Pub. Date: Dec. 5, 2019

(65) Prior Publication Data

US 2021/0213209 A1 Jul. 15, 2021

(51) Int. Cl.
*A61M 5/32* (2006.01)
*A61M 5/31* (2006.01)

(52) U.S. Cl.
CPC ........ *A61M 5/3202* (2013.01); *A61M 5/3137* (2013.01); *A61M 2005/3139* (2013.01)

(58) Field of Classification Search
CPC .............. A61M 5/3202; A61M 5/3137; A61M 5/3204; A61M 5/3213; A61M 5/3134;
(Continued)

(56) References Cited

U.S. PATENT DOCUMENTS 5,163,918 A 11/1992 Righi et al.
5,215,533 A 6/1993 Robb
(Continued)

FOREIGN PATENT DOCUMENTS

CN 105169532 A 12/2015
CN 105530980 A 4/2016
(Continued)

OTHER PUBLICATIONS

U.S. Appl. No. 29/676,220, Janssen Pharmaceuticals, Inc.
(Continued)

*Primary Examiner* — Laura A Bouchelle
*Assistant Examiner* — Sarah Dympna Grasmeder
(74) *Attorney, Agent, or Firm* — Craig M. Brown

(57) ABSTRACT

A cap for an injection device includes a removable needle boot for covering a needle of a syringe within the injection device. The cap comprises a cap body and a first boot engagement portion. The first boot engagement portion is movable relative to the cap body and comprises a first pinch portion. The first pinch portion is configured such that application of compressive force to the first pinch portion
(Continued)

effects engagement of the first boot engagement portion with the needle boot for removal of the needle boot with the cap as it is removed from the injection device.

31 Claims, 11 Drawing Sheets

(58) Field of Classification Search
CPC .. A61M 2005/3139; A61M 2205/0216; A61B 5/150534; A61B 5/150633; A61B 5/150694; A61B 5/150717
See application file for complete search history.

(56) References Cited

U.S. PATENT DOCUMENTS 6,159,184 A 12/2000 Perez et al.
6,171,283 B1 1/2001 Perez et al.
D446,578 S 8/2001 Jansen et al.
6,344,032 B1 2/2002 Perez et al.
6,623,459 B1 9/2003 Doyle
7,041,085 B2 5/2006 Perez et al.
D613,861 S 4/2010 Hunter et al.
7,824,379 B2 11/2010 Doyle
D634,424 S 3/2011 Morejon
D673,677 S 1/2013 Noda et al.
D702,835 S 4/2014 Vinchon
D720,070 S 12/2014 Khalaj
8,941,559 B2 1/2015 Bar-Zeev et al.
8,974,424 B2 3/2015 Soma et al.
D770,612 S 11/2016 Green et al.
9,522,233 B2 12/2016 Bicknell et al.
D784,524 S 4/2017 Corbin
D784,526 S 4/2017 Grunhut
D784,527 S 4/2017 Llewellyn-Hyde
D785,788 S 5/2017 Nguyen
D816,834 S 5/2018 Knight
D816,835 S 5/2018 Knight
D818,575 S 5/2018 Corbin
D819,805 S 6/2018 Knight
D830,540 S 10/2018 Rolfs et al.
10,272,202 B2 4/2019 Brereton et al.
D872,259 S 1/2020 Guo et al.
D888,941 S 6/2020 Scrimgeour et al.
D902,391 S 11/2020 Scrimgeour et al.
D902,392 S 11/2020 Scrimgeour et al.
D903,108 S 11/2020 Scrimgeour et al.
D923,776 S 6/2021 Hartman
D941,994 S 1/2022 Inoue et al.
D954,942 S 6/2022 Lee
D963,842 S 9/2022 Ratjen
D987,820 S 5/2023 Yabe
D1,004,085 S 11/2023 Mcelroy et al.
D1,034,976 S 7/2024 Schneider et al.
D1,042,804 S 9/2024 Schrul et al.
D1,071,173 S 4/2025 Liu et al.
2002/0161337 A1 10/2002 Shaw et al.
2003/0093032 A1 5/2003 Py et al.
2003/0144631 A1 7/2003 Doyle et al.
2003/0144632 A1 7/2003 Hommann et al.
2003/0187402 A1 10/2003 Doyle
2005/0033242 A1 2/2005 Perez et al.
2005/0054987 A1 3/2005 Perez et al.
2006/0036216 A1 2/2006 Rimlinger et al.
2006/0089594 A1 4/2006 Landau
2006/0106342 A1 5/2006 Cox
2006/0111679 A1 5/2006 Millerd
2007/0047200 A1 3/2007 Huang
2007/0060893 A1 3/2007 Mahurkar
2007/0073224 A1 3/2007 Dries
2007/0239117 A1 10/2007 Chelak et al.
2008/0208140 A1 8/2008 Barrelle
2008/0269692 A1 10/2008 James et al.
2008/0300549 A1 12/2008 Verespej et al.
2009/0043262 A1 2/2009 Snow
2010/0324492 A1 12/2010 Peruzzo
2011/0092915 A1* 4/2011 Olson ................ A61M 5/31511 604/198
2011/0230832 A1 9/2011 Neale et al.
2012/0232491 A1 9/2012 Jennings
2012/0238961 A1 9/2012 Julian et al.
2012/0310207 A1 12/2012 Doyle
2013/0116624 A1 5/2013 Plunnecke
2013/0144219 A1* 6/2013 Evans ................ A61M 5/3202 604/263
2013/0184655 A1 7/2013 Lanzi et al.
2013/0197446 A1 8/2013 Gustafsson et al.
2013/0289524 A1 10/2013 Crawford
2014/0039406 A1 2/2014 Verespej et al.
2014/0039407 A1 2/2014 Schoonmaker
2014/0257193 A1 9/2014 Bostrom et al.
2014/0296782 A1 10/2014 Ulrich et al.
2014/0343505 A1 11/2014 Henley et al.
2015/0174335 A1 6/2015 Roervig et al.
2015/0174340 A1 6/2015 Torris et al.
2016/0175539 A1* 6/2016 Riedel ................ A61M 5/3204 604/192
2016/0193413 A1 7/2016 Gabrielsson
2016/0325047 A1 11/2016 Vedrine et al.
2017/0014574 A1 1/2017 Ogawa
2017/0014578 A1* 1/2017 Bunch ................ A61M 5/3204
2017/0015733 A1 1/2017 Warter et al.
2017/0157332 A1 6/2017 Nguyen
2017/0157334 A1 6/2017 Nguyen
2017/0173270 A1 6/2017 Nakamura et al.
2019/0111218 A1 4/2019 Beyers et al.
2020/0164149 A1 5/2020 Mclusky et al.
2021/0030972 A1* 2/2021 Valentin .............. A61M 5/3204
2021/0290855 A1 9/2021 Mclusky et al.

FOREIGN PATENT DOCUMENTS

CN 107485763 A 12/2017
EM 004024677-0002 5/2017
EM 004024677-0003 5/2017
EM 004024677-0004 5/2017
EP 0578811 A1 1/1994
EP 2623145 8/2013
EP 2588167 2/2018
FR 3025433 3/2016
FR 3025433 A1 * 3/2016 .......... A61M 5/3204
GB 2308302 11/1997
JP D1341211 9/2008
JP D1341392 9/2008
JP D1354787 2/2009
JP 2015/62563 4/2015
JP D1557827 8/2016
JP D1558612 8/2016
JP 2016-526996 9/2016
JP D1564673 11/2016
JP D1565060 11/2016
JP 2016-540584 A 12/2016
JP D1571037 2/2017
JP D1571038 2/2017
JP D1571040 2/2017
JP D1610075 S 7/2018
JP 2020055470 A 4/2020
JP 2021-1520901 8/2021
KR 300876368 10/2016
KR 300891458 1/2017
RU 2620353 5/2017
WO WO 1995/007722 3/1995
WO WO 1999/017823 4/1999
WO WO 2001/085239 11/2001
WO WO 2004/069302 8/2004
WO WO 2007/047200 4/2007
WO WO 2008/016381 2/2008
WO WO 2010/104779 9/2010
WO 2014150201 A1 9/2014
WO WO 2015/0007857 1/2015
WO WO 2015/044561 4/2015
WO WO 2015/0091850 6/2015
WO WO 2015/122884 8/2015
WO 2016158140 A1 10/2016

(56) References Cited

FOREIGN PATENT DOCUMENTS

| | | |
|---|---|---|
| WO | WO 2017/089266 | 6/2017 |
| WO | WO 2018/075335 | 4/2018 |
| WO | WO 2018/222574 | 12/2018 |
| WO | WO 2018/222575 | 12/2018 |
| WO | WO 2019/0197381 | 10/2019 |
| WO | WO 2019/231432 | 12/2019 |

OTHER PUBLICATIONS

International Search Report dated Sep. 3, 2018; International Application No. PCT/US2018/034850.

International Search Report dated Aug. 30, 2018; International Application No. PCT/US2018/034849.

International Search Report dated Aug. 21, 2018; International Application No. PCT/US2018/034852.

International Trademark No. 1143335-S, Safety Syringes, Inc., Feb. 17, 2012.

D. Prajapati, 2015, "BD Ultrasafe Hi Res", https://www.youtube.com/watch?v=VxL1VFYAbhl.

Written Opinion, received for Singapore Application No. 1201911059S, mailed on Jan. 30, 2023, 9 pages.

* cited by examiner 190
810
340
330
310
320

CAP FOR AN INJECTION DEVICE

CROSS REFERENCE TO RELATED APPLICATIONS

This application is the U.S. national stage of PCT Application No. PCT/US2018/034852, filed May 29, 2018, the entire disclosure of which is hereby incorporated by reference in its entirety.

FIELD OF THE INVENTION

The present invention is related to the field of injection devices, specifically a cap for use with an injection device, and a cap and injection device in combination.

BACKGROUND OF THE INVENTION

Safety devices are commonly used with syringes when performing injections so as to reduce the risk of accidental needle sticks which might result in transmission of blood borne pathogens. Such safety devices are often required to protect health care providers, such as physicians and nurses, who frequently use syringes to administer injections to patients. These needle safety devices typically can be categorized as one of two types: (1) passive devices that automatically cover the needle after the injection, without requiring additional steps from the user to activate the device; and (2) devices that require an additional step to be performed by the user to activate the needle safety feature. Passive needle safety devices generally are considered to be superior in their ability to protect the user from accidental needle sticks, because, for various reasons, users may fail to take the additional actions required to activate non-passive devices. Health authorities and health care systems often require the use of needle safety devices in settings where health care providers (HCPs) perform injections. Furthermore, needle safety devices are desirable for self- and caregiver-administered injections to mitigate the risk of injury, infection, and the spread of blood borne pathogens to patients, family members, caregivers and anyone who might come in contact with the injection devices in the process of performing the injection and disposing of used syringes.

A commonly used example of manual needle safety devices is the UltraSafe® family of devices, manufactured by Becton Dickinson. A typical UltraSafe safety device consists of two plastic components and a spring that are assembled to the syringe, along with a custom plunger rod. Upon completion of the injection, the plunger rod engages latches on the UltraSafe housing components, activating the device and causing the spring to extend one of the housing components over the needle and lock into place. An example of an UltraSafe device is shown in FIGS. 1A and 1B. FIG. 1A shows the device in a ready state, before an injection takes place. FIG. 1B shown the device in a safe, used state, after an injection has been completed.

Syringes are especially difficult for patients and caregivers to use, not only because of the complexity of the steps to use the device, but also because syringes with exposed needles tend to cause anxiety for the patient. It is also desirable for such a device to be operable with one hand and in a manner which results in consistent needle insertion depth. These, and other problems, may be overcome by the use of a housing, or grip accessory.

Prior to use, and in order to avoid the risk of needle stick injury, syringes typically comprise a needle boot. A needle boot is a polymer or rubberised sheath which is received over the needle of the syringe. Often, a plastic needle boot cover is also included over the needle boot to provide a rigid support to protect the needle from bending. The needle boot cover will often comprise a friction surface or ribs so that a user may grip the needle boot cover to remove it. The needle boot is engaged with the needle boot cover such that removal of the cover also results in removal of the needle boot.

One possible difficulty with the use of a grip accessory like those described above, is that a portion of the needle boot or the needle boot cover may be covered by the grip accessory. In such an instance the difficulty of removal of the needle boot may be increased due to reduced access to the friction surface or ribs of the needle boot or boot cover. Even in the case where the grip accessory does not provide an additional obstacle to the user, the user of such a device may have difficulty in removing the needle boot and boot cover since they are unable to grip and pull the boot and cover with sufficient force for removal. This may typically be seen in users in older age groups or with medical conditions which affect dexterity and grip strength. In some cases, the user may not recognise that they need to remove the needle boot and boot cover because it is partially obscured by the housing or they might simply forget. For some needle safety devices, such as the UltraSafe family of devices, if the user fails to remove the needle boot and cover prior to using the device, the syringe will become separated from the needle safety device when the needle boot and cover are pressed against the injection site with sufficient force.

There is a need for a needle safety device which can simplify the process for and reduce the physical burden on a user in preparing the syringe for use, particularly when used with a manual syringe safety device. There is also a need for a needle safety device which makes it clear that the needle boot and cover should be removed, and which prevents failure of the device if used improperly.

SUMMARY OF THE INVENTION

In a first aspect of the invention there is disclosed a cap for an injection device including a removable needle boot for covering a needle of a syringe within the injection device, said cap comprising: a cap body; and a first boot engagement portion movable relative to the cap body, the first boot engagement portion comprising: a first pinch portion configured such that application of compressive force to the first pinch portion effects engagement of the first boot engagement portion with the needle boot for removal of the needle boot with the cap as it is removed from the injection device. The cap can provide a clear indication to the user that the needle boot needs to be removed since the cap is inherently more visible than a needle boot. The cap may also provide an easier to use clasp for a user to remove the boot.

In one embodiment, the cap further comprises a second boot engagement portion movable relative to the cap body, the second boot engagement portion comprising: a second pinch portion configured such that application of compressive force to the second pinch portion effects engagement of the second boot engagement portion with the needle boot for removal of the needle boot with the cap as it is removed from the injection device. Where the device includes a second engagement portion the boot is gripped from two sides further improving the manageability of boot removal. A second side may also be gripped by a user. Further, the first and second boot engagement portions are diametrically opposed. Such configuration allows the boot to be advantageously pinched by the cap for removal. Pinching provides a more effective removal mechanism. Furthermore, the first boot engagement portion and the second boot engagement portion are movably coupled by a hinge portion.

Optionally, the first boot engagement portion and the second boot engagement portion are resiliently deformable such that application of compressive force to the first pinch portion and the second pinch portion deforms the first boot engagement portion and the second boot engagement portion to effect engagement of the first boot engagement portion and the second boot engagement portion with the needle boot. This provides a more effective grip and clasping action on the needle boot to assist in its removal.

Optionally, the hinge portion is resiliently deformable such that application of compressive force to the first pinch portion and the second pinch portion deforms the hinge portion to effect engagement of the first boot engagement portion and the second boot engagement portion with the needle boot. Such a deformable hinge allows the engagement portions to remain relatively stiff, compared to the hinge, so as to improve the level of grip on the needle boot.

Further, the first boot engagement portion may comprise a frictious material configured to grip the needle boot. Such material improves the grip of the boot without compromising the mechanical and material features of the remainder of the cap. The second boot engagement portion may also comprise a frictious material configured to grip the needle boot.

Optionally, one or both of the first boot engagement portion and the second boot engagement portion comprises an insert of resiliently deformable frictious material configured to engage the syringe boot. By providing the material as an insert the remainder of the cap can be formed separately allowing choice of materials with properties suited to the deformation of the cap and the strength to grip the needle boot. However, the frictious material may also be overmolded onto the cap.

The frictious material may extend through the first and/or second pinch portions and form at least one rib for gripping the pinch portion. Such form of the device improves the user's grip on the portions of the cap to be engaged, improving manageability of needle boot removal. These features also can serve to indicate where the user should place their fingers when gripping the cap, and that the cap is a separable component that should be removed before performing an injection.

In a further embodiment, the first boot engagement portion is configured to contact the syringe boot at a first distance, Lc, from the hinge portion, and the first pinch portion is configured to be engaged by a user at a second distance, Lp, from the hinge portion; and wherein the second distance Lp is greater than the first distance Lc. By providing this leverage, the user may apply relatively little force to remove the cap, thereby rendering preparation of the device for injection simpler and less physically demanding.

The cap may further comprise a housing engagement portion configured to engage with a corresponding cap engagement portion of a housing for a syringe. The housing engagement portion comprises a protrusion configured to engage a corresponding cut-out in the housing for a syringe. Optionally, the housing engagement portion comprises a cut-out configured to engage a corresponding protrusion in the housing for a syringe.

Further, the housing engagement portion may be configured to retain or lock the cap within a portion of the syringe housing when the compressive force applied to the first pinch portion is below a threshold unlocking value. Advantageously the user must squeeze the cap in order to both unlock the cap and to remove the boot. This ensures that the user knows to squeeze the cap to operate the device, which means that the boot can be removed. Since the cap can be squeezed to engage the boot, the assembly of the device is much easier and requires less force. Less force in assembling the device means that the integrity of the injection device is less likely to be compromised. In particular, since the cap provides clearance for the needle boot and boot cover when it is not being squeezed, there is little or no interference with the needle boot when the syringe is assembled in the device. This eliminates the risk of compromising the integrity of the container which would be present in the case of any device in which a needle boot or boot cover must be assembled into engagement with a cap or removal means. The housing engagement portion may be configured to unlock the cap from within a portion of the syringe housing when the compressive force applied to the first pinch portion is above a threshold unlocking value.

Optionally, the housing engagement portion comprises a cam surface configured to progressively increase the compressive force to one or both of the first and second pinch portions when the cap is separated from the housing. Advantageously, the cam may provide assistance to the user in squeezing the cap to remove the boot. Alternatively such a surface may make it easier for the user to pull the cap from the injection device.

Furthermore, one or both of the first pinch portion and the second pinch portion may comprise at least one rib such that the pinch portion is tactile. One or both of the first pinch portion and the second pinch portion may also comprise an outwardly extending ridge. Advantageously, the rib and/or the outwardly extending ridge may provide more grip for the user in the proximal cap removal direction. Such improved grip reduces the amount of squeezing or compression of the walls by the user to that which is suitable for unlocking the cap from the housing. It is beneficial that the amount of squeezing required by the user to unlock the cap is similar to or slightly more than the amount of squeezing required to grip the cap to remove it from the housing.

Optionally, the cap may further comprise at least one retaining clip and at least one corresponding retaining surface, wherein the retaining clip is configured to engage with the retaining surface such that the first boot engagement portion remains engaged with the needle boot after compressive force has been removed from the first pinch portion. Advantageously the boot is then retained within the cap and is less likely to be dropped once removed. Fewer components for the user to deal with improves the manageability of the device in use. The cap may comprise two retaining clips and two corresponding retaining surfaces.

Further to the above, the two retaining clips may be disposed on the first sidewall and the two corresponding retaining surfaces are disposed on the second sidewall. Optionally, a first one of the retaining clips is disposed on the first sidewall, a first one of the retaining surfaces is disposed on the second sidewall, a second one of the retaining clips is disposed on the second sidewall, and a second one of the retaining surfaces is disposed on the first sidewall. Each one of the at least one retaining clips may comprise a tine. Advantageously, the length of engagement between the cap and the housing stabilises the cap with respect to the housing so that the cap along with the needle boot are easily removed axially and prevents the user rotating the boot or trying to remove it off-axis. Off-axis removal or rotating the boot can cause bending of the needle.

In another embodiment, the cap further comprises at least one tab configured to engage and retain the needle boot within the cap. Advantageously the boot is then retained within the cap and is less likely to be dropped once removed. Fewer components for the user to deal with and handle thus improves the manageability of the device in use. The first boot engagement portion may comprise a first rib configured to abut the second boot engaging portion such that deflection of the first boot engagement portion is limited. Limiting the movement of the boot engaging portions can prevent over squeezing of the device which may actually restrict removal of the cap from the device by flexing portions of the cap to be in contact with the housing. Advantageously the ribs also provide visual and tactile feedback that the cap has been squeezed the sufficient amount. Optionally, the second boot engagement portion may also comprise a second rib configured to abut the first rib such that deflection of the first boot engagement portion and the second boot engagement portion is limited.

In a further embodiment, there is provided a grip accessory for a syringe, comprising: a housing configured to retain a syringe; and a cap as described in any of the aspects above. The grip accessory may further comprise a syringe.

In one further embodiment of the invention there is provided a manual injection device comprising the grip accessory as described above.

BRIEF DESCRIPTION OF THE DRAWINGS

The present invention is described with reference to the accompanying figures in which:

FIG. 7 is a cross-sectional view of the cap of FIGS. 5A-C;

DETAILED DESCRIPTION

The present invention is described in exemplary form with reference to the specific disclosure set out below made in relation to the accompanying figures.

Whilst the exemplary embodiments are depicted in relation to a manual injection device, the skilled person understands that a cap according to the invention may be used with a variety of injection devices where boot removal is required. Such injection devices may be manual injection devices, grip accessories which support manual injection devices, or automatic injection devices (e.g. autoinjectors) in which one or more of needle penetration and actuation of the plunger may be carried out automatically by a drive system. The benefits of a cap according to the invention can thus be realised with numerous types of injection devices where boots need to be removed.

Figures 1A, 1B:
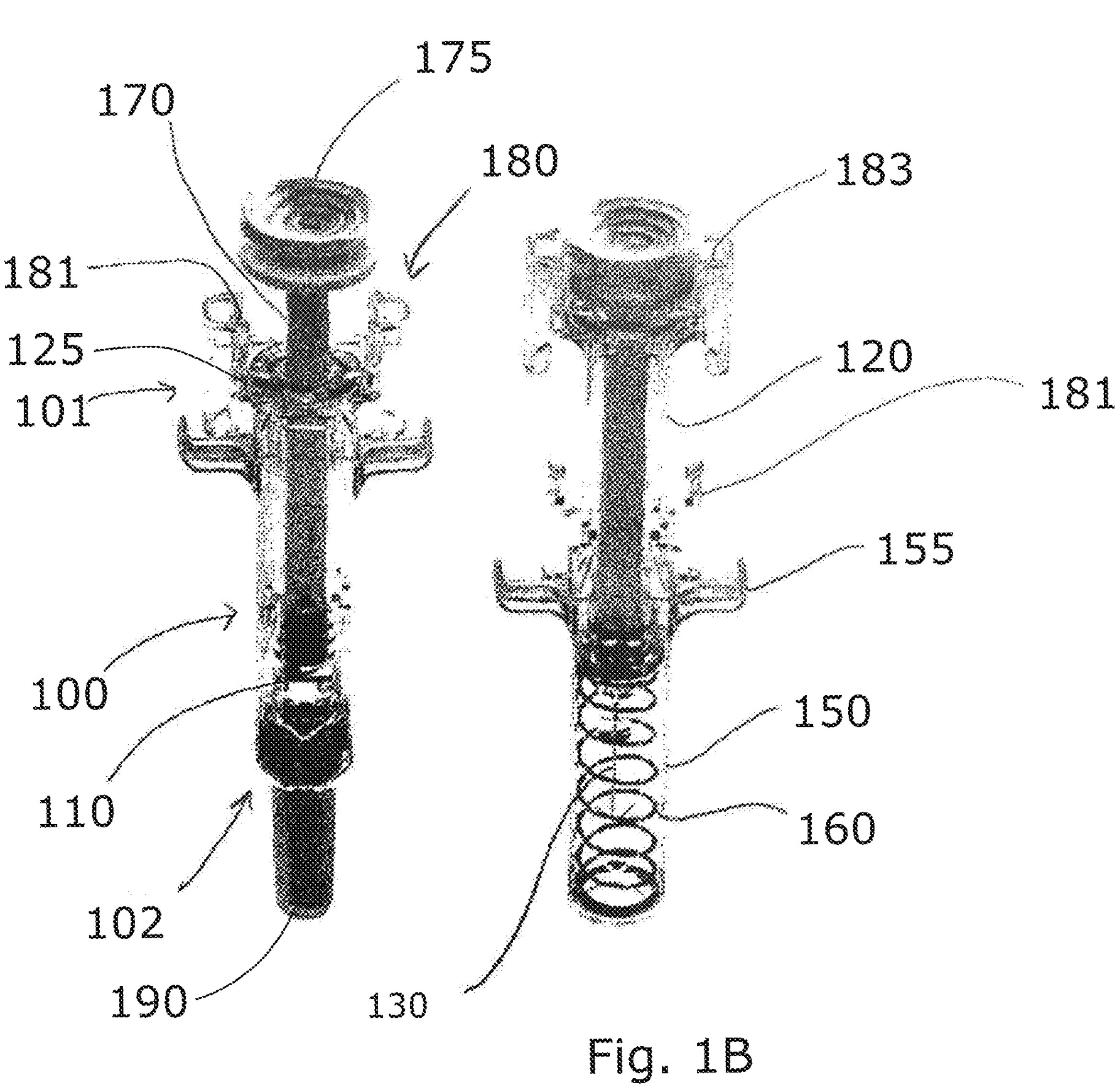
FIGS. 1A-1B show conventional manual injection device in an injection ready state (FIG. 1A), and a safe, post-injection state (FIG. 1B)

FIGS. 1A-B show a manual injection device 100 that is suitable for use with a grip accessory and cap according to the present invention. The injection device 100 comprises a syringe 110, which extends from a proximal end comprising a needle 130, to an open distal end. The open distal end of the syringe is sealed by a bung. A needle boot 190 is optionally provided to sheath the needle 130.

The syringe 110 is secured within a syringe sheath 120 by a syringe locking element 125. The syringe locking element 125 may comprise diametrically opposed abutment surfaces between which the flange of a standard syringe is confined. The confinement of the flanges between abutment surfaces prevents movement of the syringe 110 relative to the syringe sheath 120.

The syringe sheath 120 comprises an open distal end, into which the syringe 110 can be inserted, and an open proximal end, from which the needle 130 extends when the syringe 110 is secured within the sheath 120. A safety shield 150 is movably mounted with respect to the syringe sheath 120. The safety shield 150 is movable between a retracted position (shown in FIG. 1A), in which the needle 130 extends beyond the proximal end of the safety shield, and an extended position (shown in FIG. 1B), in which the safety shield extends beyond the proximal end of the needle. In the second position shown in FIG. 1B, the needle 130 is covered by the safety shield 150, thereby shielding the user from the needle and preventing accidental needle-stick injuries.

To allow the user to grip the injection device 100 with a conventional dart grip, the safety shield 150 comprises flanges 155 at or towards its distal end. The flanges 155 shown in FIG. 1 extend from the safety shield 150. However, the skilled person will appreciate that the flanges 155 can be provided on the syringe sheath 120.

The safety shield 150 is biased into its extended position relative to the syringe sheath 120 (shown in FIG. 1B) by a biasing element 160. The biasing element 160 shown in FIGS. 1A-B takes the form of a coil spring arranged between the syringe sheath 120 and the safety shield 150 such that the safety shield 150 is biased proximally relative to the syringe sheath 120 into its extended position.

A releasable locking mechanism 180 retains the safety shield 150 in its retracted position relative to the syringe sheath 120. The locking mechanism 180 is movable between a locked position, in which the locking mechanism 180 prevents the safety shield 150 moving relative to the syringe sheath 120 (FIG. 1A), and an unlocked position in which the locking mechanism 180 no longer prevents movement of the safety shield 150 relative to the syringe sheath 120. Once the locking mechanism is moved to its unlocked position, the safety shield 150 moves to its extended position under the influence of the coil spring 160 (FIG. 1B).

In the device shown in FIGS. 1A-B, the locking mechanism 180 between the safety shield 150 and the syringe sheath 120 takes the form of a pair of flexible latch arms 181 provided on the safety shield 150, which engage opposing latching surfaces 183 on the syringe sheath 120. The flexible latch arms 181 are biased into a first position in which they engage their respective latching surfaces 183, thus preventing proximal movement of the safety shield 150 relative to the syringe sheath 120. When the flexible latch arms 181 are moved against this bias, the latch arms 181 disengage their respective latching surfaces 183, thus permitting proximal movement of the safety shield 150 relative to the syringe sheath 120.

The latch arms 181 are configured to be moved from the first position to the second position by a custom plunger rod 170. The plunger rod 170 comprises an elongate member, configured at its proximal end to engage the bung 140 and move the bung proximally along the longitudinal axis of the syringe body to deliver a dose of medicament through the needle 130. At or towards its distal end, the plunger 170 is provided with an actuation surface 175 on which the user can place a thumb or finger to drive the plunger proximally to deliver the injection. As the plunger rod nears or reaches the end of its travel within the syringe body, the actuation surface 175 of the plunger rod 170 deflects the flexible latch arms 181 outwardly, to a position in which they no longer engage the latching surfaces 183 on the syringe sheath 120. The locking mechanism is thus released at the end of the injection and the safety shield 150 moves to its extended position.

Although not visible in the accompanying drawings, the manual injection device of FIGS. 1A-B can additionally comprise a safety lock for locking the safety shield 150 in its extended position after the injection has been completed.

A grip accessory for use with the injection device of FIGS. 1A and 1B will now be described with reference to FIG. 2.

Figure 2:
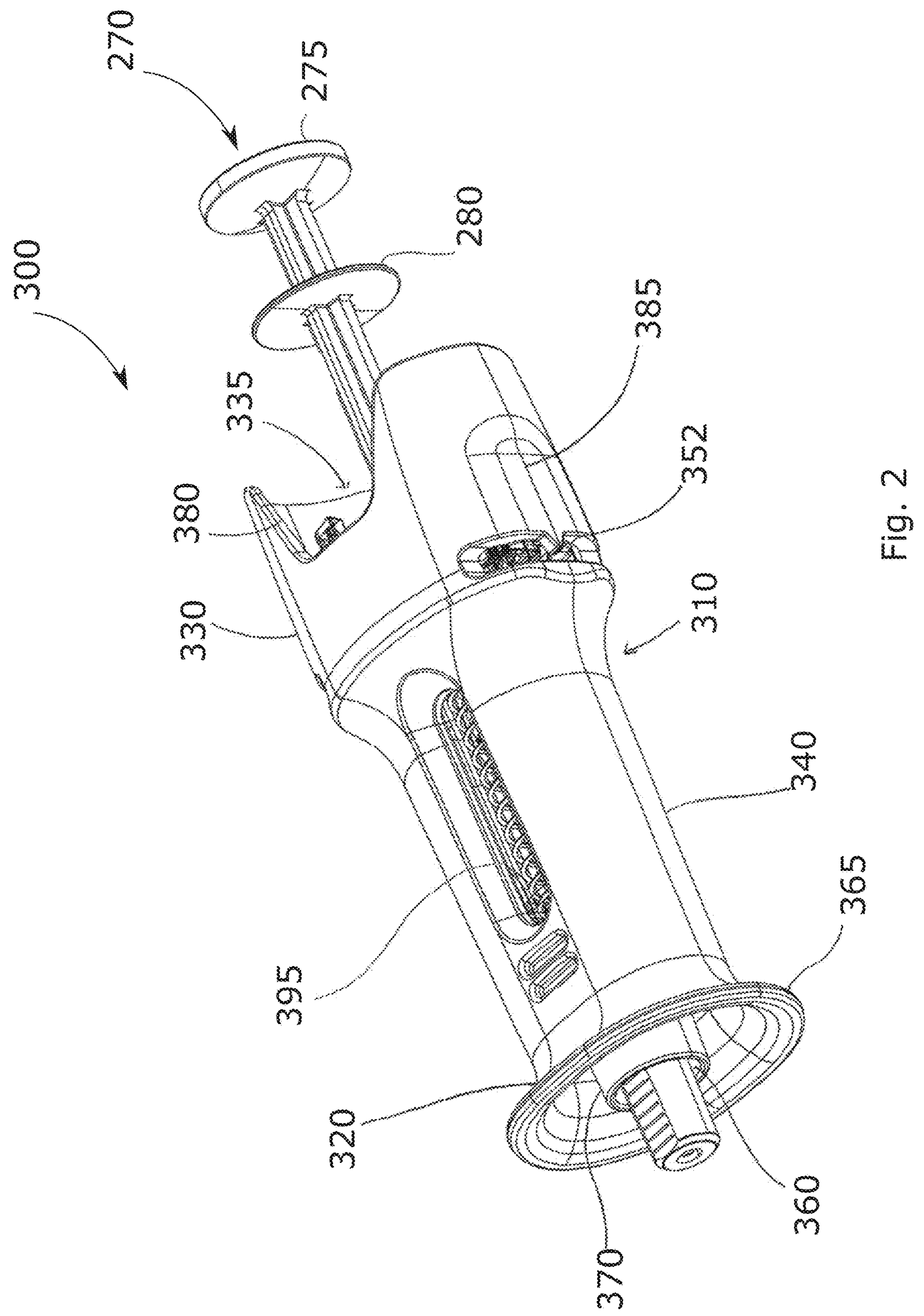
FIG. 2 shows a grip accessory housing the injection device of FIGS. 1A-B.

As shown in FIG. 2, the grip accessory 300 comprises a housing 310, having a distal portion 330, a proximal portion 320 and an intermediate portion 340 extending between the proximal and distal portions. The distal portion 330 of the housing 310 comprises a distal opening 335 to allow insertion of the injection device into the generally hollow body. Proximal of the distal opening, the housing 310 comprises two recesses 352 that confine the flanges 155 of the safety shield 150 and secure the injection device 100 within the housing. With the flanges 155 confined in recesses 352, the syringe 110 and needle 130 are fixed relative to the grip accessory 300 until locking mechanism 180 is released.

To facilitate insertion of the injection device 100 into the housing 310, ramped surfaces (not shown) may be provided on an interior of the housing 310 immediately distal of the recesses 352, which guide the flanges 155 of the injection device 100 into the recesses 352. Once the flanges 155 ride over ramps (not shown) and snap into recesses 352, the injection device 100 is locked into the grip accessory 300. In some aspects, although not all, the housing further comprises ribs on the interior of the housing, for preventing lateral and rotational movement of the injection device 100 within the housing 310.

As shown in FIG. 2, the distal portion 330 of the housing 310 can at least partially surround the locking mechanism 180 of the injection device 100 to provide a shield around the locking mechanism 180 of the injection device 100. The shield prevents the user's hand from coming into direct contact with the locking mechanism 180 and inadvertently moving the releasing locking mechanism 180 and activating the needle shield before the injection is complete. To allow the user to view the distal end of the injection device 100, the distal portion 330 may comprise one or more cut-outs 380. The cut-outs 380 also provide space for the plunger rod to clear the housing without preventing the plunger rod from being depressed should the user push substantially sideways on the plunger rod whilst injecting.

In various embodiments, a grip accessory is provided with a housing cap of the present invention. The housing cap can be configured to at least partially close the proximal opening of the grip accessory. Preferably, the housing cap comprises a sheath for enclosing a needle boot of the injection device. The housing cap can be configured such that the needle boot is removed from the needle simultaneously with the housing cap. This can be achieved by providing engagement features on an interior surface of the housing cap that grip the needle boot or the needle boot cover during removal.

In some embodiments, the housing cap can comprise at least one engagement feature for engaging corresponding engagement feature(s) on the housing of the grip accessory. The engagement features secure the housing cap in position at the proximal end of the grip accessory housing.

The engagement features on the housing cap can comprise one or more locking tabs on an exterior surface of the housing cap. The engagement features on the grip accessory housing can comprise locking grooves on an interior of the housing, dimensioned to receive the locking tabs.

In some embodiments, the generally hollow body of the grip accessory housing can comprise guide means for guiding the locking tabs into the corresponding locking grooves. For example, the guide means comprise channels extending proximally from the locking grooves and can be dimensioned to receive the locking tabs and guide the tabs towards the locking grooves. The locking tabs can comprise a distal bevelled edge to guide the locking tabs into the locking grooves. Alternatively, the locking grooves could be provided on the housing cap and the locking tabs provided on the grip accessory housing.

Figures 3A, 3B:
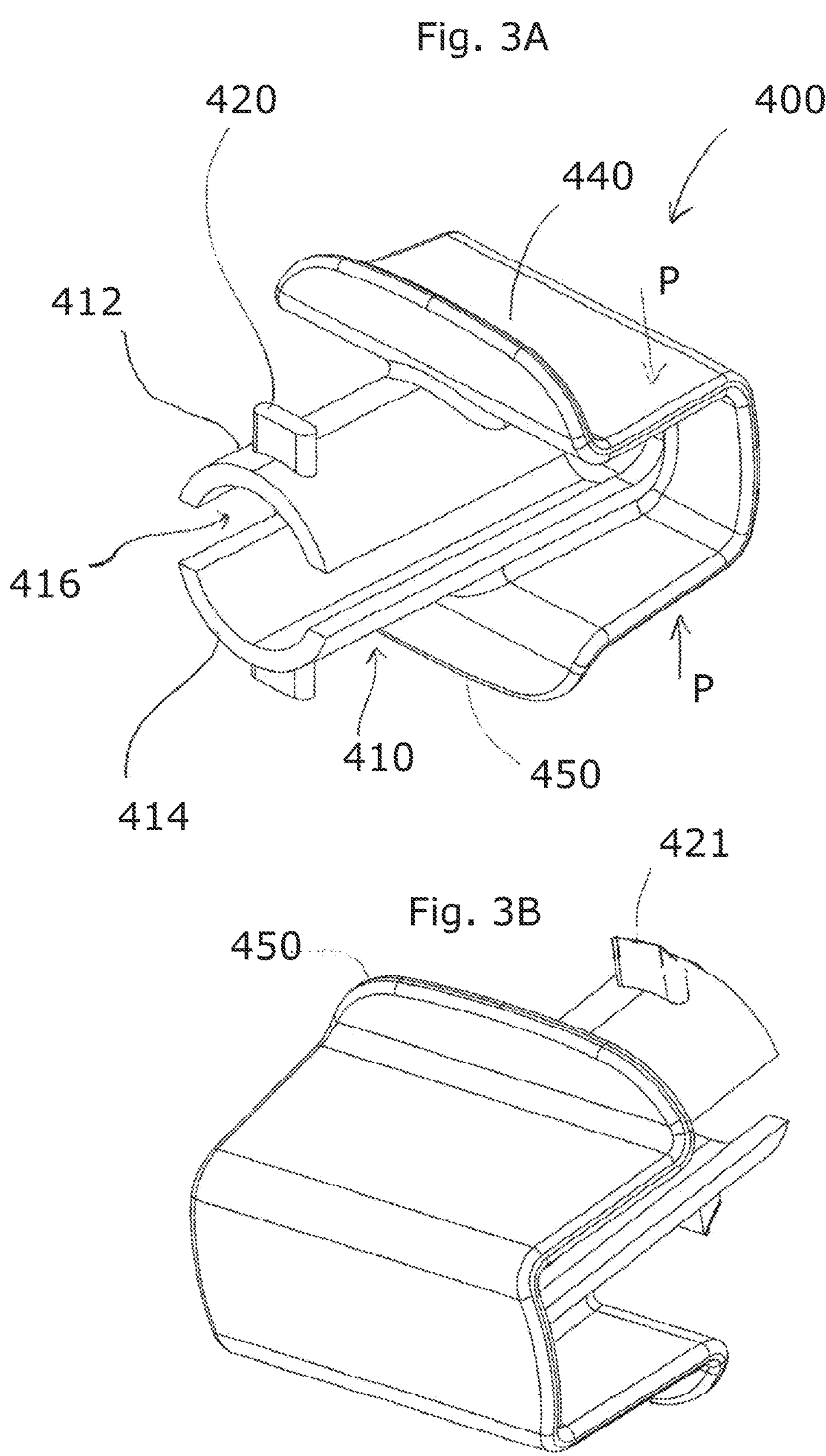
FIGS. 3A-3B are perspective views of a cap of a first embodiment suitable for use with the injection device of FIGS. 1A-B according to the invention.
Figure 4:
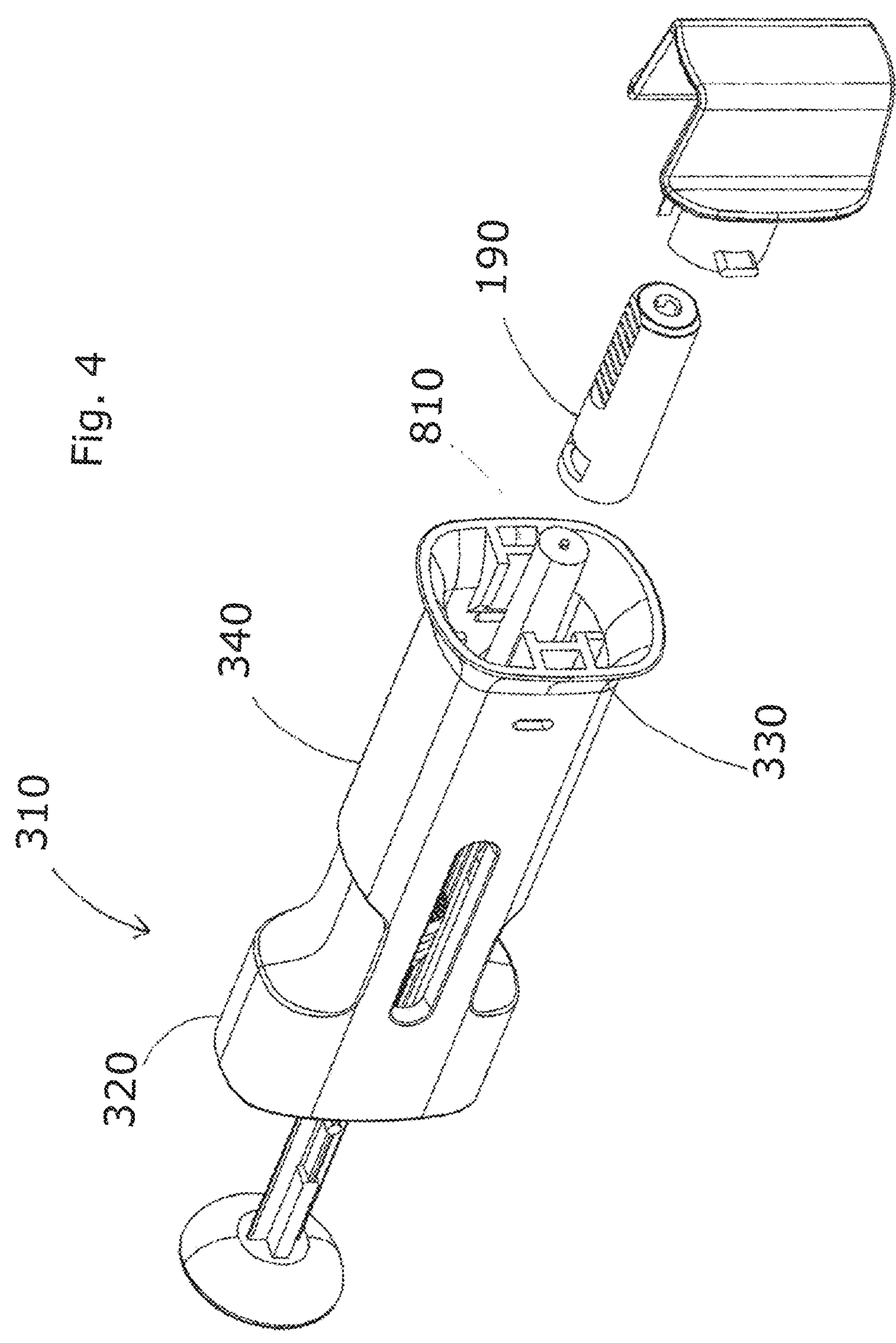
FIG. 4 is an exploded view of the cap of FIGS. 3A-B in conjunction with the injection device of FIGS. 1A-B.

Referring now to FIGS. 3A-B and FIG. 4, grip accessories may be provided with a housing cap 400 according to a first embodiment of the present invention. The housing cap 400 is configured to sheath the needle 130 and the needle boot 190 of the injection device 110. As shown in FIG. 4, the housing cap 400 extends from and closes the proximal opening 360 of the housing 310. Removal of the housing cap 400 from the grip accessory 300 removes the needle boot 190 from the needle, thereby readying the injection device 110 for injection. Because the housing cap 400 is clearly visible on the proximal portion 320 of the housing 310, the housing cap 400 prevents misuse of the device by failure to remove the needle boot 190, which the user often cannot always easily see in grip accessory 310. Further improvement of visibility of the housing cap 400 may be achieved by providing the housing cap 400 in a colour which contrasts with that of the body of the grip accessory. As a non-limiting example, a blue housing cap provided in combination with a white or pale coloured grip accessory provides an improved visual indication that the housing cap 400 should be removed from the device prior to use.

The housing cap 400 will now be described in more detail with reference to FIGS. 3A and 3B. As shown in FIGS. 3A and 3B, the housing cap 400 comprises a sheath 410 partially split along its length to form a first sidewall 412 and a second sidewall 414, separated by cut-outs 416. The first and second sidewalls 412, 414 generally form a cavity for receiving a needle assembly comprising a needle 130 and a needle cap 190, with needle cap engaging means, such as a plurality of claws or a resiliently deformable portion including a frictious surface, for securing the needle cap 190 within the housing cap 400. However, the skilled person will recognise that the cavity of housing cap 400 may be provided with an integral needle boot for sealing the needle 130 of an injection device. In any case, removal of the cap 400 is configured to unsheathe the needle ready for insertion into the injection site.

The housing cap 400, and in particular the first and second sidewalls 412, 414 are formed of a resiliently flexible material such that the first and second sidewalls 412, 414 can be moved from a first position to a second position when a force F is applied to the first and second sidewalls, as shown in FIG. 3A. Application of the force P by a pinching motion moves the first and second sidewalls 412, 414 towards each other. In the embodiment shown in FIGS. 3A and 3B, movement of the first and second sidewalls towards each other is possible due to the cut-outs 416 separating the two sidewalls. However, the skilled person will understand that other arrangements are possible that allow the first and second sidewalls to flex inwardly toward each other. For example, in alternative embodiments, the cap 400 may comprise a sheath 410 in which the cutouts 412, 414 are replaced with a material of higher flexibility relative to the first and second sidewalls 412, 414. Other means of providing a squeezable cap will be apparent to a person skilled in the art.

As shown in FIGS. 3A and 3B, the first sidewall and the second sidewall each comprise at least one housing engagement feature, such as a locking tab 420 on the outer surface of each of the first and second sidewalls 412, 414. The locking tabs 420 are configured to cooperate with one or more corresponding cap engagement features 430 on an interior surface of the housing 310. The cap engagement features on the housing 310 may take the form of a locking groove 430 sized to receive the locking tab 420 provided on the housing cap 400. Of course, the skilled person will appreciate that the locking tabs 420 can instead be provided on the grip accessory housing 310, with the corresponding grooves 430 for receiving the locking tabs located on the cap 400.

As shown in FIG. 3B, in some (although not all) embodiments, the locking tabs 420 may comprise bevelled distal edges 421 to help guide and deflect the locking tabs 420 into the corresponding locking features on the housing during assembly.

As shown in FIGS. 3A and 3B, the cap 400 may further comprise grip surfaces 440. The grip surfaces are coupled to or integrally formed with the first and second sidewalls 412, 414 such that pressure applied to the grip surfaces 440 deflects the first and second sidewalls 412, 414 to their second position. In the preferred embodiment shown in FIGS. 3A-B, the grip surfaces are generally planar, opposing surfaces. This provides a greater surface area for gripping and ensures that the pinching force is applied correctly to deflect the first and second sidewalls towards each other. In some embodiments, the grip surfaces 440 may also comprise a surface feature, such as a ridged area, to further aid gripping of the housing cap 400.

The locking tabs 420 can include bevelled edges to facilitate replacement of cap, if desired. The bevelled edges of the locking tabs 420 guide the locking tabs into position into the corresponding locking grooves on the housing.

As shown in FIGS. 3A-B, the cap 400 may also comprise a flange 450 extending from the first and second grip surfaces 440 that closes the aperture at the proximal end of the grip accessory housing.

As shown in FIG. 4, in embodiments of the grip accessory provided with a housing cap 400, the grip accessory 300 may further comprise guide means 810 for guiding the locking tabs 420 into the corresponding cap engagement features on the housing. As shown in FIG. 4, the guide means can comprise a groove extending proximally from the cap engagement feature in the housing along which the locking tabs 420 can slide towards the cap engagement feature.

Figures 5A, 5B, 5C:
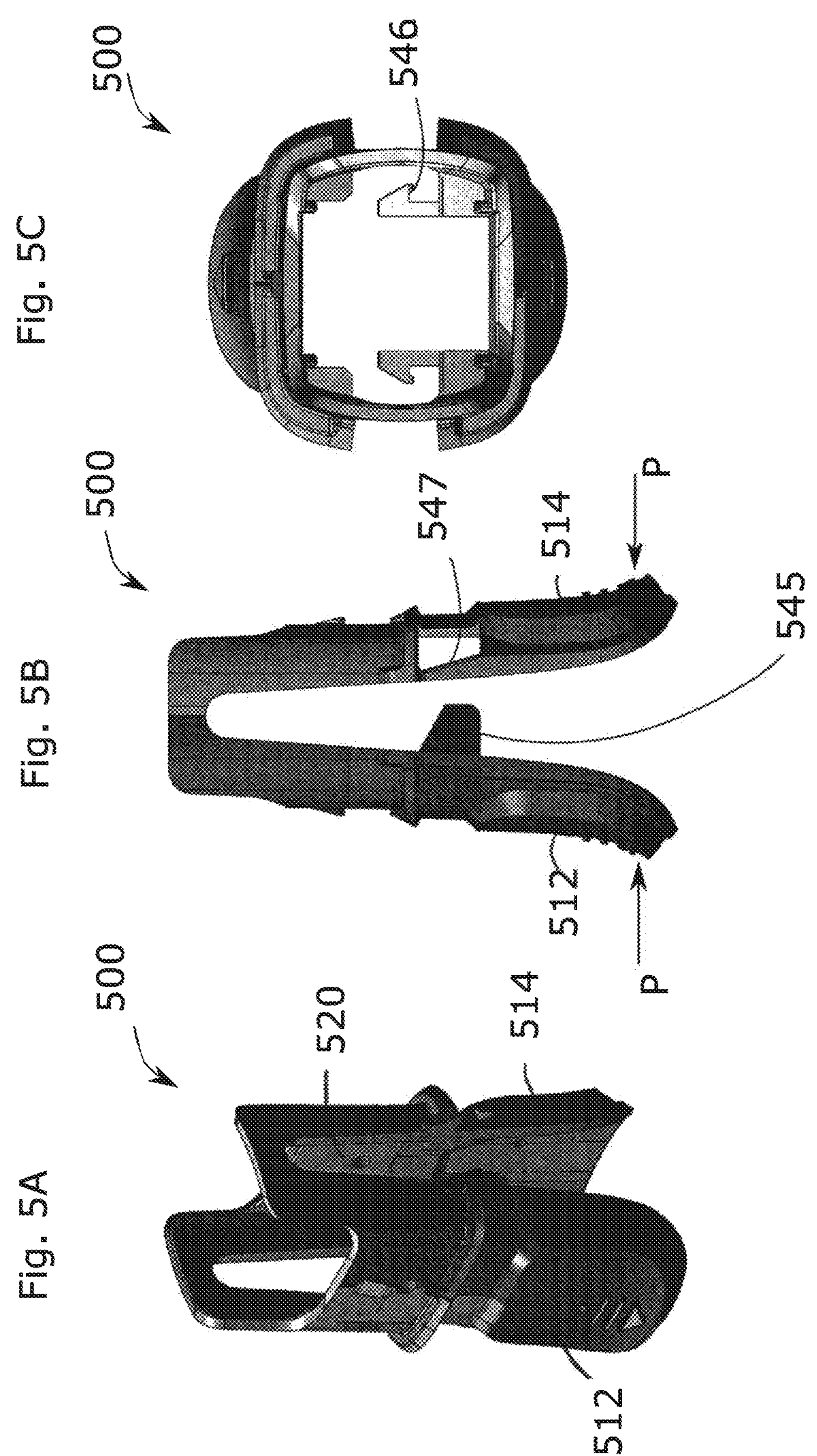
FIGS. 5A-5C are side, top and perspective views of a cap of a second embodiment suitable for use with the injection device of FIGS. 1A-B according to the invention.

A second embodiment of a housing cap 500 according to the present invention is shown in FIGS. 5A-5C. In the embodiment of FIGS. 5A-5C, the housing cap 500 comprises first and second sidewalls 512, 514 formed of a resiliently flexible material such that the first and second sidewalls 512, 514 can be moved from a first position to a second position when a pinching force P is applied to the first and second sidewalls, as shown in FIG. 5B.

Application of the force P by a pinching motion moves the first and second sidewalls towards each other. Movement of the first and second sidewalls 512, 514 towards one another is possible because of the cut-outs which separate the first and second sidewalls and provide space for the first and second sidewalls to move. As the first and second sidewalls move together, an engagement portion 520 is configured to engage with a needle boot or a needle boot cover which is disposed within the central channel defined by the first and second sidewalls on either side.

Figure 6A:
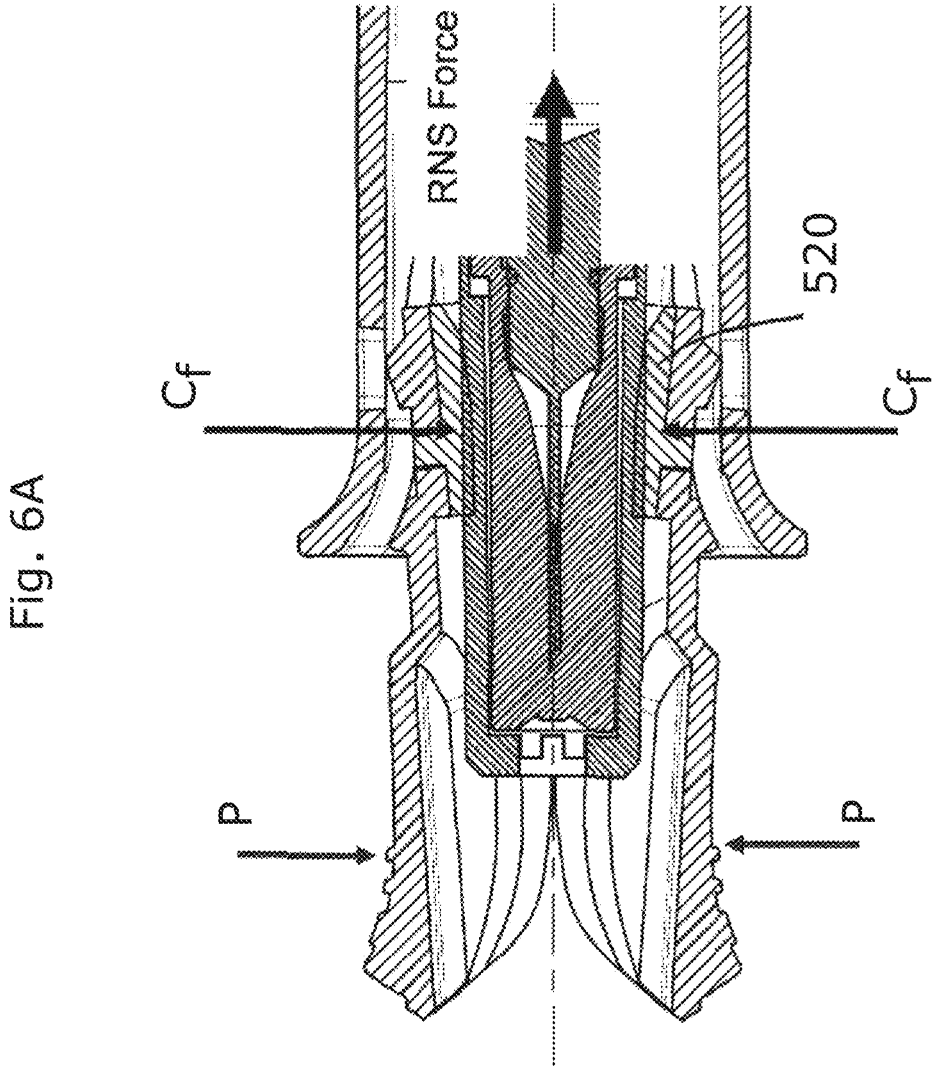
FIGS. 6A-6B are cross-sectional views of the cap of FIGS. 5A-C in use.
Figure 6B:
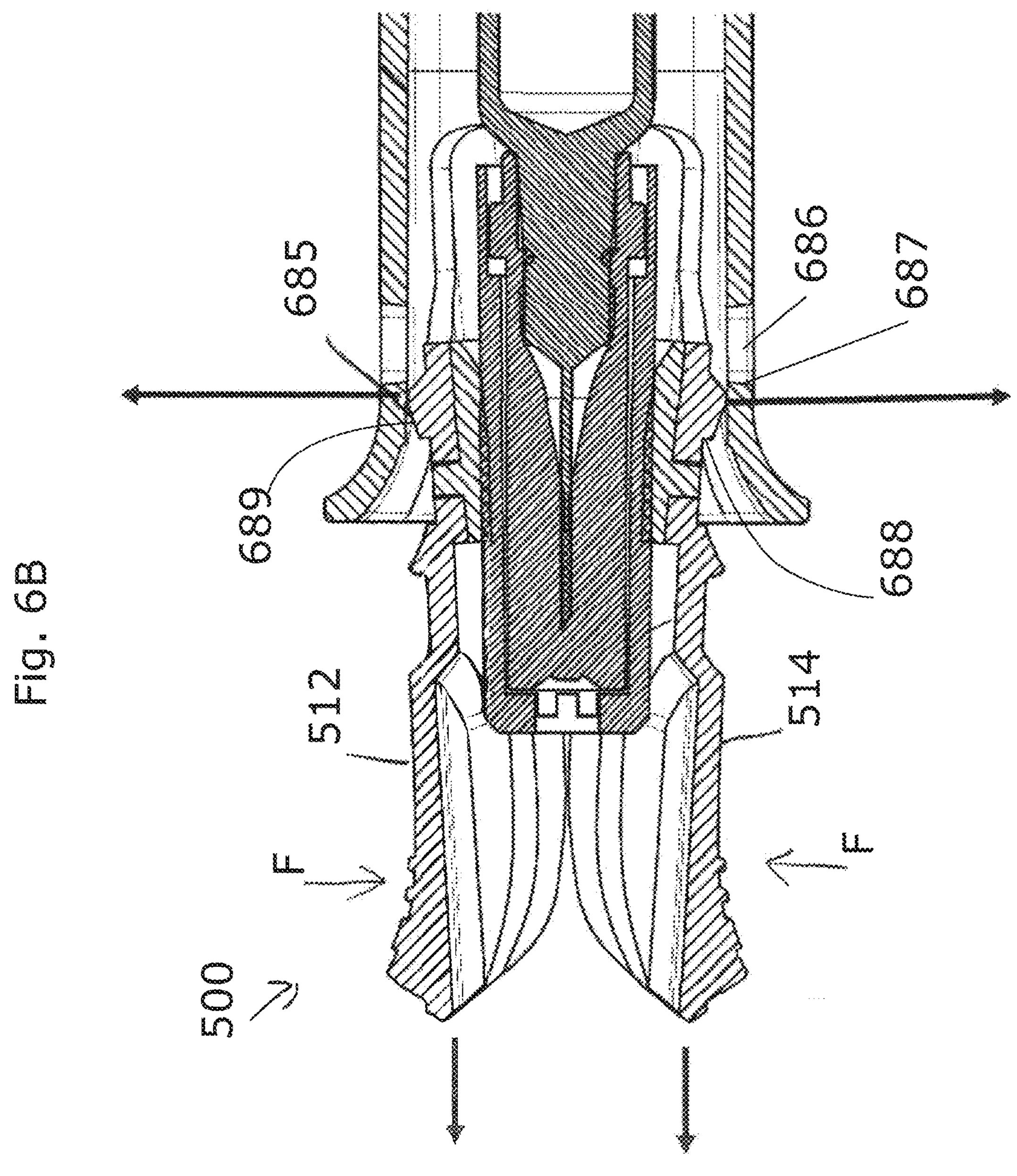
Figure 7:
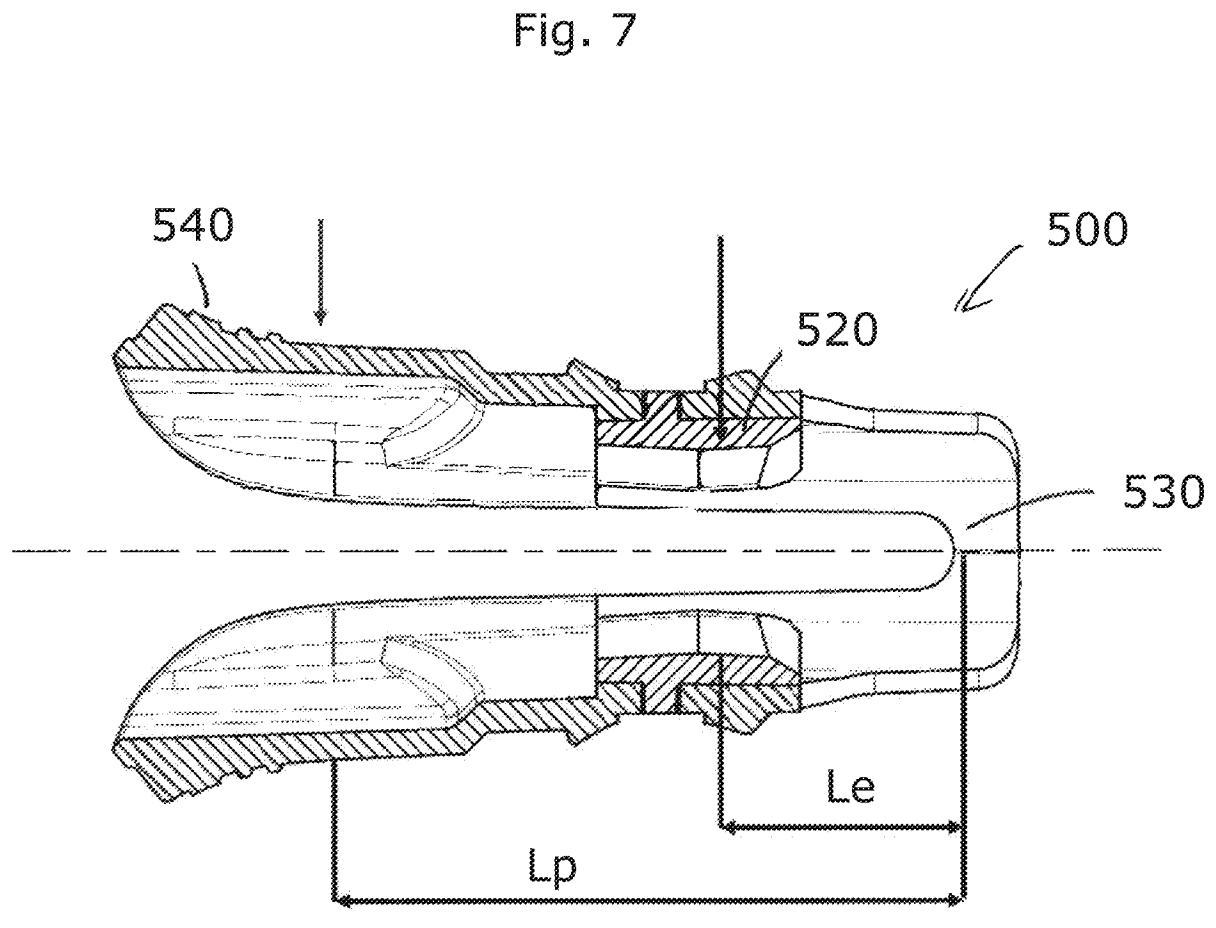

Now with reference to FIGS. 6A-6B, it can be seen that the housing cap 500 is configured such that the application of the pinching force P provides a mechanical advantage over the contact force Cf which is applied by the engagement portion 520. The mechanical advantage may be more readily understood with reference to FIG. 7; the housing cap is shown in section view, the section being made at a plane of symmetry of the housing cap 500. At the distal end of the housing cap (the right hand side of FIG. 7) the first and second sidewalls converge at a hinge portion 530. The first and second sidewalls effectively "pivot" or flex about the hinge portion by a lever action applied to the pinch portion 540. The pinch portion of the housing cap is located at a point on the first and/or second sidewalls a distance Lp from the hinge portion 530. The engagement portion 520 is configured to engage the syringe boot or syringe boot cover at a distance Le from the hinge portion. Since the engagement portion 520 and the pinch portion 540 move substantially together around the hinge portion in a pivoting manner, the moment applied at the pinch portion 540 is equal to the moment applied by the engagement portion 520 to the needle boot or needle boot cover. The distance Lp of the pinch portion from the hinge portion 520 is greater than the distance Le of the engagement portion from the hinge portion, and so the force actually applied by the engagement portion engaging the needle boot or needle boot cover is greater than the force applied by a user to the pinch portion.

It will be understood that the engagement portion may be formed separately from but assembled with the housing cap. However, alternatively, the engagement portion could be formed contiguously with the housing cap or comprise a portion of the housing cap. Furthermore, the engagement portion may be made from the same material as the housing cap, or alternatively the engagement portion may be made from a different material than the housing cap. Where the material of the engagement portion is different than that of the housing cap, it will be understood that a resilient material such as rubber or an elastomer may be chosen such that the friction of engagement is increased. In preferred embodiments, where the engagement portion is configured to engage a needle boot cover which is typically stiffer than a needle boot, the engagement portion is formed from a softer material, such as rubber or an elastomer; where the engagement portion is configured to engage a needle boot itself, which is typically formed of an elastomer, the engagement portion is formed from a resilient polymer. In either case, one of the engagement portion and either the needle boot or needle boot cover is formed from a stiffer material and the other is formed from a less stiff, resiliently deformable material.

In the second embodiment, as shown in FIG. 6A, one or both of the first and second sidewalls comprises a pip 685 on the external surface of the one or both of the first and second sidewalls. The pip 685 or pips are configured to engage a complimentary recess 686 on the interior of the housing of the grip accessory. When the first and second sidewalls are resiliently biased into the first position, the pips 685 are engaged with the recess 686 such that they hold the housing cap in place and prevent it from being removed from the grip accessory. The pips include a locking surface 688 which engages with a complimentary recess locking surface 687 to prohibit movement of the cap proximally out of the housing. The pips 685 are configured such that when the pinching force P is applied to the first and second sidewalls they do not prevent the housing cap from being removed. The locking surface of the pip and the complimentary recess locking surface are engaged when the first and second sidewalls are in the first position and are no longer engageable when the first and second sidewalls are pinched together. In this way, the pips 685 function to hold the housing cap on the device prior to purposeful removal for use of the device.

As shown in FIG. 6A, the pips are also configured such that they increase the contact force applied to the needle cap. The pips comprise a camming surface 689 which is configured to engage the interior surface of the grip accessory progressively as the housing cap is removed from the grip accessory. The slope of the camming surface is provided such that the progressive increase in contact force during removal of the housing cap is predetermined. An increase in the angle of the slope provides for a higher rate of increase in contact force applied as the housing cap is removed. Such a camming action acting to further close the first and second sidewalls together and further increase the contact force applied to the needle cap lessens the force required by the user to pinch together the first and second sidewalls.

Additionally, the camming action of the pips to increase the contact force provides for a finer control of the contact force without burden to the user to apply the correct force. Whilst it may be that a user struggles to apply a consistent and great enough pinch force to apply a suitable contact force without the pips, with the pips, the ultimate contact force has a partial dependency on the size and configuration of the pips.

Now with reference to both FIGS. 6A and 6B, the process of removing the cap of the present invention will be described. In use, when a user applies a pinching force P to the first and second sidewalls, the first and second sidewalls move or flex inwardly against a resilient bias provided by a hinge portion of the housing cap. The hinge portion of the housing cap comprises a portion specifically intended to deform such that the first and second sidewalls may move together. The hinge portion is formed from the same material and contiguously with the first and second sidewalls. Alternatively, the skilled person would understand that any other form of hinged connection may be used, for example the hinged portion may comprise a mechanical hinge including bearing surfaces or a living hinge which plastically deforms to provide flexibility.

In FIG. 6A the first and second sidewalls have been pinched together, but the cap has not yet been proximally removed from the housing. Turning to FIG. 6B, the cap is at a second stage where the user has begun to remove the cap from the housing. The needle boot and needle boot cover have been partially removed from the needle, but not entirely. As the user continues to pull the housing cap proximally, the camming surfaces of the pips engage the interior surface of the housing applying further force to the first and second sidewalls tending to bias the first and second sidewalls to grip the needle boot cover and needle boot with a greater force. At this point, if the user were to reduce effort in pinching together the first and second sidewalls in an attempt to pull the cap proximally with more force, the cap will tend to assist in gripping the needle boot and needle boot cover to compensate for the reduced pinching effort.

As shown in FIG. 5B and FIG. 5C, the first sidewall includes a clip 545 which has a retaining tine 546. The second sidewall includes a corresponding retaining surface 547 which is engageable with the tine 546 of the clip to retain the first and second sidewalls in the second pinched position once a threshold deflection due to pinching of the first and second sidewalls has been reached. The embodiment of FIGS. 5B and 5C shows two clips on the first sidewall and two retaining surfaces on the second sidewall, although it will be appreciated that any number of clips and corresponding retaining surfaces may be employed to a similar effect. Similarly, the housing cap may comprise a clip on the first sidewall and a clip on the second sidewall, each with a corresponding retaining surface on the opposite sidewall. In use, once the clips have been retained by the retaining surface the first and second sidewalls of the housing cap remain in engagement with the needle boot cover and needle boot such that a user need not continue to apply pinching force to engage the needle boot cover and needle boot.

Figure 8:
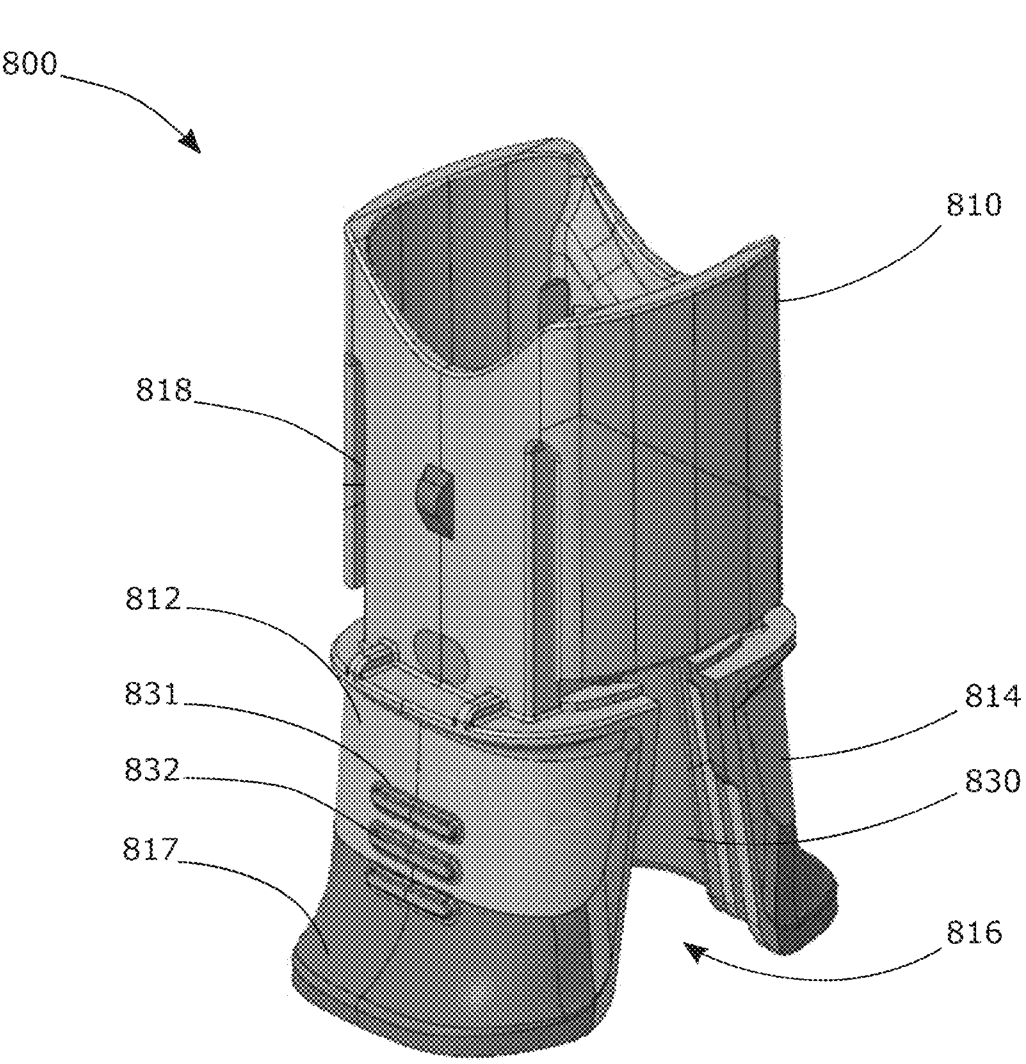
FIG. 8 is a top perspective view of a cap of a third embodiment suitable for use with the injection device of FIGS. 1A-B according to the invention.

In a third embodiment, as shown in FIG. 8, there is provided a housing cap for an injection device. The housing cap of the third embodiment is similar to the housing cap of the second embodiment, but is additionally configured as described below. The housing cap 800 comprises a sheath 810 partially split along its length to form first sidewall 812 and second sidewall 814 separated by cut-outs 816. In addition to the cut-outs provided in the sheath separating the first sidewall 812 and the second sidewall 814, each sidewall is further separated from the body of the sheath by a pair of longitudinal slots 818. The longitudinal slots allow for the cantilever action of the first and second sidewalls to extend further along the body of the sheath.

Additionally, with reference to FIG. 8, the first and second sidewalls comprise, at their proximal ends, a flared or laterally extending portion 817. The flared portion 817 provides an additional reaction surface for a user to grip even after the first and second sidewalls have been deflected together.

The first sidewall 812 and the second sidewall 814 also each comprise a rubbery gripping surface 830. The rubbery gripping surface 830 may be overmolded onto an interior surface of each sidewall. Alternatively the rubbery gripping surface may be formed separately from the rest of the housing cap and then fixed to the housing cap with an adhesive, for example, or by a press fit. The housing cap may also comprise one or more receptacles 831 configured to receive a portion of the rubbery gripping surfaces thereby increasing the adhesion or the retention of the rubbery gripping surface in the housing cap. In the case of overmolding the rubbery gripping surface, the receptacles 831 may also provide a passage for the material to form the rubbery gripping surface to be injected for overmolding. Additionally, the receptacles may provide for some of the rubbery gripping surface to extend through the sidewall and protrude to provide ribs 832 or protrusions to enhance the grip for pulling the housing cap from the housing.

Figure 9:
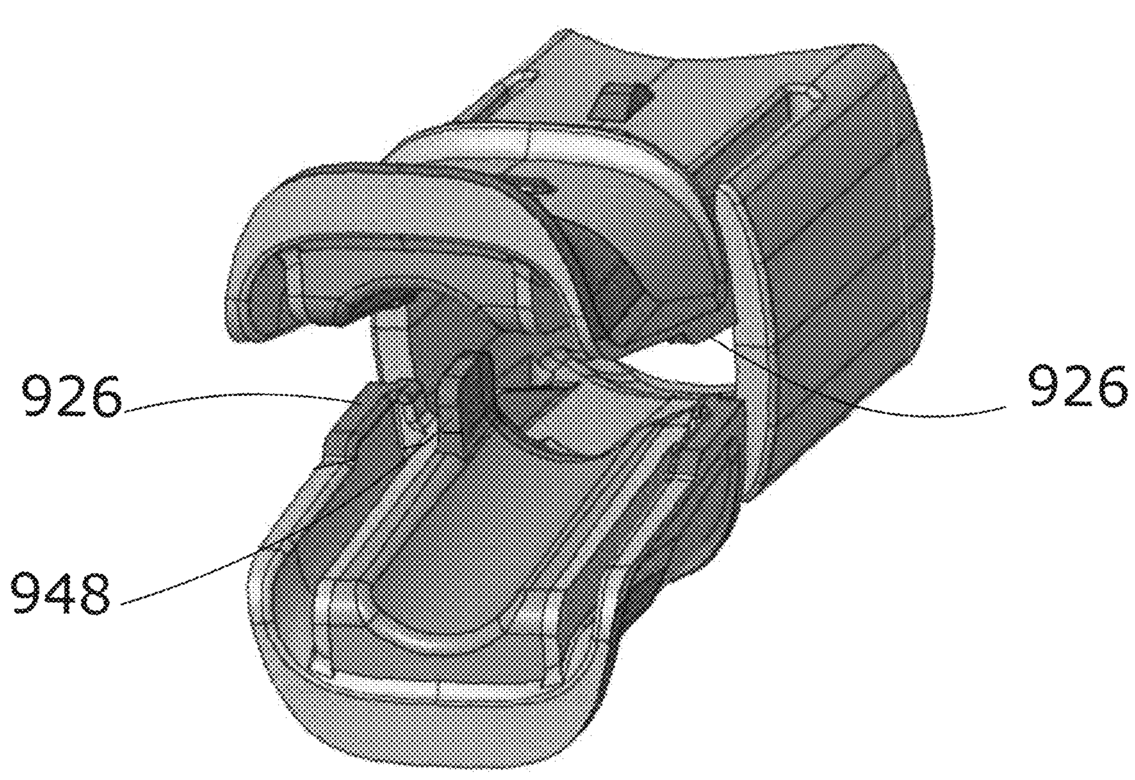
FIG. 9 is a side perspective view of the cap of FIG. 8.

Now, looking at FIG. 9, a rib 926 extends from an interior edge or interior surface of at least one of the first and second sidewalls. Optionally, a second rib 926 also extends from an opposing interior edge or interior surface of the other of the first and second sidewalls. The rib 926 or ribs extend such that when the two sidewalls deflect together one rib 926 engages with either the opposing sidewall or, if a second rib 926 is present, with the opposing rib 926. In this way, the motion of the two sidewalls together is obstructed, preventing over-compression of the sidewalls. Over-compression of the sidewalls may occur if a user grips the housing cap too tightly. When the housing cap is over-compressed once the needle boot has engaged the sidewalls, instead of simply flexing inwardly to engage the needle boot, further compression of the sidewalls at a proximal end causes the sidewalls to flex or curve around the needle boot. As the sidewalls flex around the needle boot, the distal ends of the sidewalls project outwardly away from a central axis of the housing cap. Such outward projection can cause the sidewalls to engage with an interior surface of the housing and resist or prevent the housing cap from being removed from the housing. By providing the rib or ribs at a location more proximal than the point of engagement with the needle boot the outward projection of the sidewalls is reduced or eliminated, mitigating the trapping effect of the housing on the housing cap.

The rib or ribs also provide enhanced feedback to the user that the sidewalls have been sufficiently compressed for removal of the needle boot. This is achieved by visual feedback: the user is able to see that the ribs have contacted when it is more difficult to see whether the needle boot has been sufficiently engaged. This is also achieved by mechanical feedback: when the ribs are engaged they provide resistance to compression of the sidewalls which is firmer or stiffer than the resistance from engagement with the needle boot or needle boot cover. The stiffer response to compression is readily detectable by a user and provides an indication that the sidewalls have been sufficiently compressed.

Also with reference to FIG. 9, the cap comprises at least one retention tab 948 extending from a sidewall of the housing cap. The cap may also comprise a second retention tab 948 extending from either the same or the opposite sidewall of the housing cap. In either case, the second retention tab 948 extends from a sidewall and is diametrically opposed to the first retention tab 948, with respect to the needle boot and boot cover, such that the retention tabs 948 are engaged with the needle boot cover. The retention tab 948 or tabs are configured such that when the needle boot has been removed and the sidewalls are no longer being compressed, the retention tabs 948 remain in engagement with the needle boot cover such that the needle boot is retained captive in the housing cap.

Figure 10C:
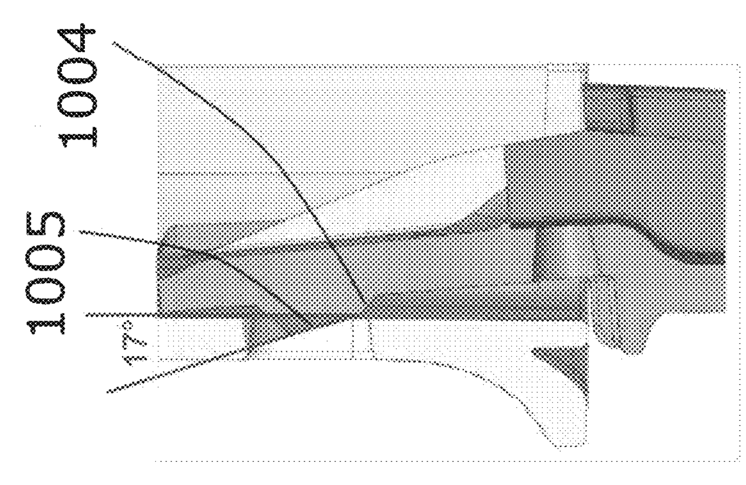
FIGS. 10A-C are cross-sectional views of the cap of FIG. 8 depicting alternative pip cross-sections.
Figure 10B:
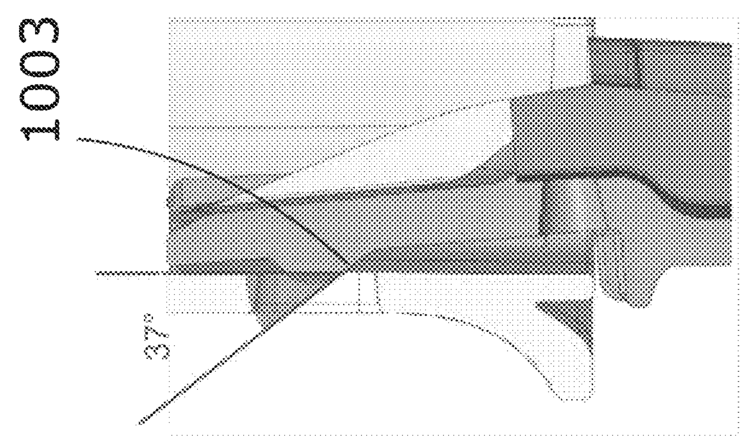
Figure 10A:
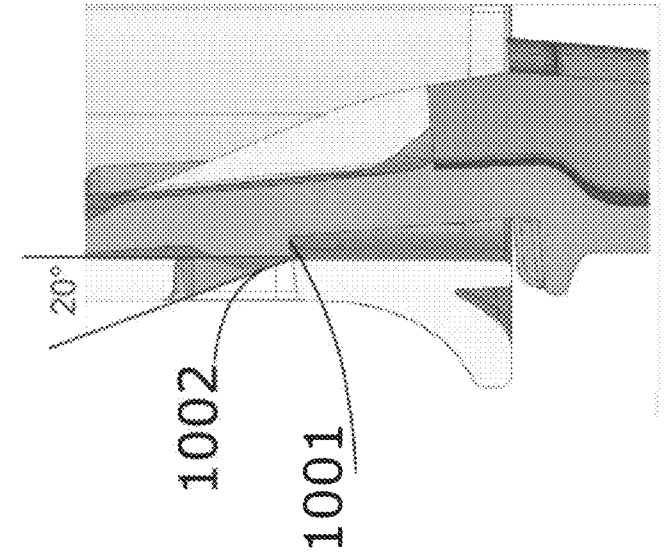

With reference now to FIG. 10, various exemplary embodiments of the pip will be described. A first embodiment of a pip is shown in FIG. 10A. Similarly to the pip described above, the pip in FIG. 10A comprises a locking surface 1001 and a camming surface 1002. The locking surface 1001 extends perpendicularly from the outer surface of the sidewall and therefore blocks removal of the housing cap from the housing. Since the locking surface 1001 extends perpendicularly, a force pulling the housing cap from the housing alone will not unlock the pip from the complementary recess in the housing. Only compression of the sidewalls together a pre-determined amount will allow some movement of the housing cap out of the housing. Once the sidewalls have been compressed together the pre-determined distance, pulling of the housing cap from the housing causes the camming surface 1002 of the pip to engage with an interior edge of the complementary recess. The slope of the camming surface may cause the sidewalls to compress slightly more than the pre-determined unlocking compression as the housing cap is withdrawn from the housing or the user may continue to manually compress the sidewalls. As the housing cap is removed further from the housing, the pip may engage with an interior surface of the housing, maintaining the level of compression of the sidewalls until the pip emerges from the proximal end of the housing. The experience for the user during the removal process is that a high level of compression is required to initially remove the needle boot, but once the initial removal stage has been completed, the compression required by the user is relaxed whilst the needle boot will still be removed with the housing cap. The axial position of the pip on the housing cap and the length between the complementary recess and the proximal end of the interior surface of the housing determine the removal length over which the pip maintains compression of the sidewalls. The removal length may be determined so that the pip maintains the compression until after the needle boot has been removed sufficiently that no or little force retaining the needle boot on the syringe remains.

A second embodiment of a pip is shown in FIG. 10B. The pip of FIG. 10B differs from the pip of FIG. 10A in that it does not include a perpendicular locking surface. The pip of FIG. 10B includes a camming surface 1003 which extends from the sidewall surface to the tip of the pip. The angle of the camming 1003 surface is chosen such that it prevents accidental removal of the housing cap or locks the housing cap in place. In an exemplary embodiment, the angle of the camming surface is 37°. In the embodiment of FIG. 10B, the camming surface 1003 is continuous, that is, there are no sharp edges or discontinuities in the camming surface. A continuous camming surface provides for smooth removal of the housing cap from the housing, since discontinuities or sharp edges may create additional resistance.

Now turning to the embodiment of FIG. 10C, the camming surface of the pip is split into two discontinuous sections. The first section encountered by the interior edge of the complementary recess is a first steep locking surface 1004. The first surface is not disposed perpendicular to the sidewall but is steep enough that the housing cap will not be accidentally removed. Once the sidewalls have been manually compressed and removal of the housing cap has begun, the interior edge of the complementary recess reaches the discontinuity and the relatively shallower second surface 1005. The angle of the second surface provides less resistance to the removal of the housing cap and may progressively increase the compression applied to the sidewalls as the housing cap is removed. The discontinuous camming surface provides an exact point at which the housing cap is "unlocked" and may be readily pulled from the housing. Such tactile feedback helps a user of the device to understand the process of using the device.

In all embodiments which comprise one or more pips, the pips may or may not contribute to the compression of the sidewalls. In particular, where the pips do not contribute to the compression of the sidewalls, the size and shape of the pip is configured such that the cap will only become unlocked for removal from the injection device once the user has applied compression to the sidewalls which is sufficient for removal of the needle boot and boot cover.

The present invention has been described above with reference to the accompanying drawings by way of example only.

The invention claimed is:

1. A cap for an injection device, wherein the injection device includes a removable needle boot for covering a needle of a syringe within the injection device, and a syringe housing for housing the syringe, said cap comprising:
- a cap body;
- a housing engagement portion configured to be received in an opening of the syringe housing through which the needle extends and engage with a corresponding cap engagement portion of the syringe housing to retain the cap within the opening of the syringe housing; and
- a first boot engagement portion movable relative to the cap body, the first boot engagement portion comprising:
  - a first pinch portion configured to, when the housing engagement portion is received in the opening of the syringe housing and a compressive force is applied to the first pinch portion, both 1) move the first boot engagement portion to engage with the needle boot and 2) move the housing engagement portion to disengage from the housing such that the cap is configured to cause removal of the needle boot from the needle when the cap is removed from the injection device.

2. The cap of claim 1, further comprising a second boot engagement portion movable relative to the cap body, the second boot engagement portion comprising:
- a second pinch portion configured to engage the second boot engagement portion with the needle boot upon application of a compressive force to the second pinch portion.

3. The cap of claim 2, wherein the first boot engagement portion and the second boot engagement portion are diametrically opposed.

4. The cap of claim 2, wherein the first boot engagement portion and the second boot engagement portion are movably coupled by a hinge portion.

5. The cap of claim 4, wherein the first boot engagement portion and the second boot engagement portion are resiliently deformable such that application of a compressive force to the first pinch portion and the second pinch portion deforms the first boot engagement portion and the second boot engagement portion to effect engagement of the first boot engagement portion and the second boot engagement portion with the needle boot.

6. The cap of claim 4, wherein the hinge portion is resiliently deformable such that application of compressive force to the first pinch portion and the second pinch portion deforms the hinge portion to effect engagement of the first boot engagement portion and the second boot engagement portion with the needle boot.

7. The cap of claim 4, wherein the first boot engagement portion is configured to contact the needle boot at a first distance, Lc, from the hinge portion,
- wherein the first pinch portion is configured to be engaged by a user at a second distance, Lp, from the hinge portion; and wherein the second distance Lp is greater than the first distance Lc.

8. The cap of claim 2, wherein the first boot engagement portion comprises a frictious material configured to grip the needle boot.

9. The cap of claim 8, wherein the second boot engagement portion comprises a frictious material configured to grip the needle boot.

10. The cap of claim 9, wherein one or both of the first boot engagement portion and the second boot engagement portion comprises an insert of resiliently deformable frictious material configured to engage the needle boot.

11. The cap of claim 9, wherein the frictious material is overmolded onto the cap.

12. The cap of claim 11, wherein the frictious material extends through the first pinch portion and/or the second pinch portion and forms at least one rib configured to grip the first pinch portion and/or the second pinch portion.

13. The cap of claim 2, wherein one or both of the first pinch portion and the second pinch portion comprises a tactile pinch portion having at least one rib.

14. The cap of claim 2, wherein the first boot engagement portion comprises a first rib configured to abut the second boot engaging portion to limit deflection of the first boot engagement portion.

15. The cap of claim 14, wherein the second boot engagement portion comprises a second rib configured to abut the first rib to limit deflection of the first boot engagement portion and the second boot engagement portion.

16. The cap of claim 1, wherein the housing engagement portion comprises a protrusion configured to engage a corresponding cut-out in the syringe housing.

17. The cap of claim 1, wherein the housing engagement portion comprises a cut-out configured to engage a corresponding protrusion in the syringe housing.

18. The cap of claim 1, wherein the housing engagement portion is configured to retain the cap within a portion of the syringe housing when the compressive force applied to the first pinch portion is below a threshold unlocking value.

19. The cap of claim 18, wherein the housing engagement portion is configured to unlock the cap from within the portion of the syringe housing when the compressive force applied to the first pinch portion is above the threshold unlocking value.

20. The cap of claim 19, wherein the housing engagement portion comprises a cam surface configured to progressively increase the compressive force to the first pinch portion when the cap is separated from the syringe housing.

21. The cap of claim 1, further comprising at least one retaining clip and at least one corresponding retaining surface, wherein the at least one retaining clip is configured to engage with the at least one corresponding retaining surface such that the first boot engagement portion remains engaged with the needle boot after compressive force has been removed from the first pinch portion.

22. The cap of claim 21, wherein the cap comprises two retaining clips and two corresponding retaining surfaces.

23. The cap of claim 22, further comprising a first sidewall and a second sidewall, wherein the two retaining clips are disposed on the first sidewall and the two corresponding retaining surfaces are disposed on the second sidewall.

24. The cap of claim 23, wherein a first one of the retaining clips is disposed on the first sidewall, a first one of the retaining surfaces is disposed on the second sidewall, a second one of the retaining clips is disposed on the second sidewall, and a second one of the retaining surfaces is disposed on the first sidewall.

25. The cap of claim 21, wherein each one of the at least one retaining clips comprises a tine.

26. The cap of claim 1, further comprising at least one tab configured to engage and retain the needle boot within the cap.

27. A grip accessory for a syringe, comprising:

the syringe housing configured to retain the syringe; and the cap according to claim 1.

28. A manual injection device comprising the grip accessory of claim 27, the needle boot, and the syringe.

29. The cap of claim 1, wherein the cap body defines a sheath configured to receive the needle boot, and the first boot engagement portion is cantilevered to the sheath.

30. The cap of claim 1, wherein the housing engagement portion is biased in an outward direction away from a central axis of the syringe housing when the compressive force is not applied to the first pinch portion.

31. The cap of claim 1, wherein the cap is configured such that application of the compressive force along an inward direction towards a central axis of the syringe housing causes the housing engagement portion to move along the inward direction to disengage from the corresponding cap engagement portion of the housing.

* * * * *